US006547943B1

United States Patent
Kane et al.

(10) Patent No.: US 6,547,943 B1
(45) Date of Patent: Apr. 15, 2003

(54) CAPILLARY SYSTEM PROVIDING MULTIPLE ANALYSIS OF SAMPLE FROM SAME BODY OF LIQUID

(75) Inventors: Thomas E. Kane, State College, PA (US); Li Qingbo, State College, PA (US)

(73) Assignee: Spectrumedix LLC, State College, PA (US)

( * ) Notice: Subject to any disclaimer, the term of this patent is extended or adjusted under 35 U.S.C. 154(b) by 0 days.

(21) Appl. No.: 09/577,479

(22) Filed: May 25, 2000

(51) Int. Cl.[7] .................... G01N 27/26; G01N 27/447
(52) U.S. Cl. ................................. 204/453; 204/604
(58) Field of Search .................. 204/451, 452, 204/453, 454, 455, 601, 602, 603, 604, 605; 356/344

(56) References Cited

U.S. PATENT DOCUMENTS

| | | | |
|---|---|---|---|
| 5,045,172 A | * 9/1991 | Guzman | 204/452 |
| 5,439,578 A | * 8/1995 | Dovichi et al. | 204/603 |
| 5,675,155 A | * 10/1997 | Pentoney, Jr. et al. | 250/458.1 |
| 5,741,411 A | 4/1998 | Yeung et al. | 204/452 |
| 5,885,430 A | * 3/1999 | Kernan et al. | 204/453 |
| 5,900,132 A | 5/1999 | Keenan et al. | 204/603 |
| 5,900,934 A | * 5/1999 | Gilby et al. | 356/344 |
| 5,916,428 A | 6/1999 | Kane et al. | 204/601 |
| 6,027,627 A | 2/2000 | Li et al. | 204/603 |
| 6,048,444 A | 4/2000 | Takahashi et al. | 204/603 |
| 6,054,032 A | 4/2000 | Haddad et al. | 204/451 |
| 6,325,908 B1 | * 12/2001 | Imai et al. | 204/603 |
| 6,331,441 B1 | * 12/2001 | Balch et al. | 436/518 |

FOREIGN PATENT DOCUMENTS

| | | |
|---|---|---|
| EP | 1089 073 A2 | 4/2001 |
| WO | WO 94/29712 | 12/1994 |
| WO | WO 98/14773 | 4/1998 |

OTHER PUBLICATIONS

International Search Report for PCT/US01/16769 filed May, 23, 2001.

* cited by examiner

Primary Examiner—Nam Nguyen
Assistant Examiner—John S. Starsiak, Jr.
(74) Attorney, Agent, or Firm—Pennie & Edmonds LLP

(57) ABSTRACT

The present invention provides capillary an electrophoresis system and method for multiple simultaneous analysis of a sample. The system and method of the invention allow the ends of a plurality of capillaries to simultaneously contact a single body of electrophoresis sample contained in a compartment of a container, such as a sample contained in a well of a micro-titer tray.

27 Claims, 4 Drawing Sheets

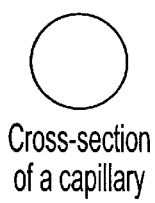
Cross-section of a capillary
Cross-section of an electrode
*Fig. 3a*
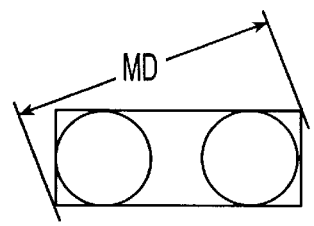
*Fig. 3b*
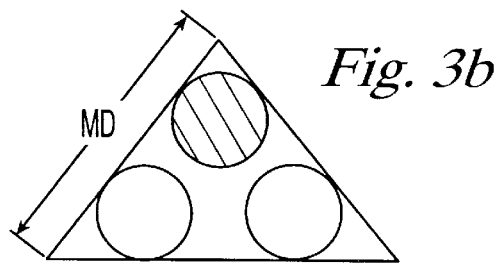
*Fig. 3c*
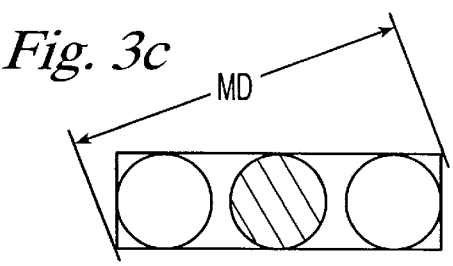
*Fig. 3d*
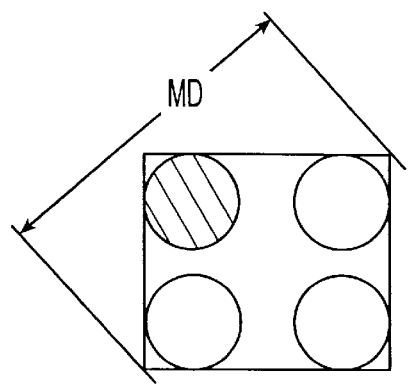
*Fig. 3e*
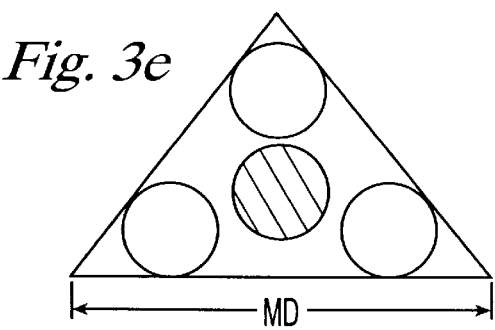
*Fig. 3f*
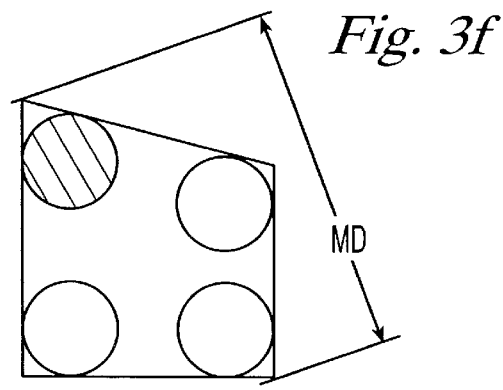
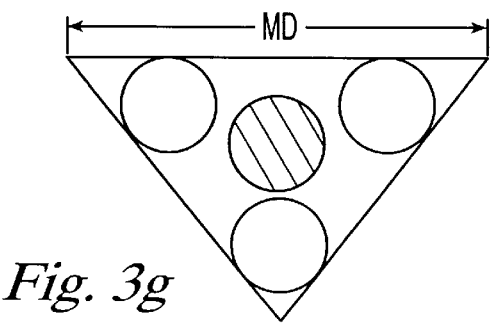
*Fig. 3g*
*Fig. 3h*
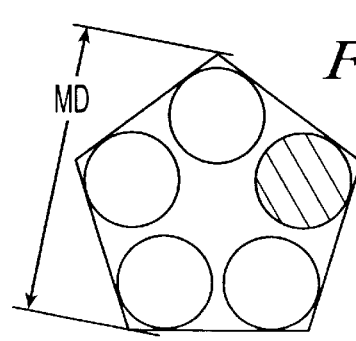

CAPILLARY SYSTEM PROVIDING MULTIPLE ANALYSIS OF SAMPLE FROM SAME BODY OF LIQUID

FIELD OF THE INVENTION

The present invention relates to a capillary electrophoresis system and method. Specifically, the invention relates to a capillary electrophoresis system and method that provides multiple simultaneous analysis of a sample by positioning first ends of a plurality of capillaries in a single container such that the plurality of capillaries provide simultaneous electrophoretic analysis for a sample in the container.

BACKGROUND OF THE INVENTION

Electrophoresis is a well-known technique for separating small amount of macromolecules. Increasingly, electrophoresis has become an indispensable tool for the biotechnology and other industries and is used extensively in a variety of applications, including the separation, identification and preparation of samples of nucleic acids, proteins and carbohydrates. Of increasing interest in the broader field of electrophoresis is capillary electrophoresis (CE), where particular entities of species are moved through a medium in an electrophoretic channel of capillary dimensions under the influence of an applied electric field. In some applications, the medium in the capillary electrophoretic channel is a buffer. Oftentimes, however, the medium is a gel which acts as a sieving matrix to help retard and separate the individual molecules as they migrate through the capillary channel.

Capillary electrophoresis is typically performed using fused silica capillary tubes. The tubes may have inner channel diameters in the range of about 20–1000 micrometers or microns ($\mu m$). Capillary electrophoresis is generally employed to analyze an extremely small quantity of samples, such as proteins or nucleic acids. Other benefits of CE include rapid run time and high separation efficiency. A capillary electrophoresis system or apparatus usually charges a glass capillary having an inner diameter of not more than 100 $\mu m$ with a migration medium such as buffer or gel, introduces a sample into an end of the capillary, and applies a high voltage across the capillary to separate molecules based on differences in charge-to-size ratio. Since capillaries have large surface area relative to their small volume, resulting in high cooling efficiency, high voltages can be applied in analyzing small quantities of samples at high speed and in high resolution.

To illustrate a capillary electrophoresis process, one may take the example of DNA sequencing using gel capillary electrophoresis. Prior to the electrophoresis analysis, the DNA sample is prepared, using well-known methods, so that a solution of DNA fragments of all possible lengths corresponding to the same total sequential order is obtained, with each fragment terminated with a tag label corresponding to the identity of the given terminal base.

The separation process employs a capillary tube filled with conductive gel. To introduce the sample, one end of the capillary channel is placed into the DNA reaction vial. After a small amount of sample enters the capillary end, both capillary ends are then placed in separate buffer solutions. A voltage potential is then applied across the capillary tube. The voltage drop causes the DNA sample to migrate from one end of the capillary to the other. Differences in the migration rates of the DNA fragments cause the sample to separate into bands of similar-length fragments. As the bands traverse the capillary channel, the bands are typically read at some point along the channel using one of several detection techniques.

Usually, multiple DNA preparation reactions are performed in a commercially available micro-titre tray having many separate low-volume wells, each holding on the order of 200–1000 micro-liters ($\mu L$). The micro-titre trays come in standard sizes. In the biotech industry, the currently preferred micro-titre tray has a rectangular array comprising 8 rows of 12 columns of wells. The centers of adjacent wells found in a single row are separated by approximately 0.9 cm, although this figure may vary by one or two tenths of a millimeter. The same holds for the spacing between adjacent wells in a single column. The rectangular array of 96 wells has a footprint within an area less than 7.5 cm×11 cm.

Miniaturization has allowed more wells to be accommodated in a single micro-titre tray having the same footprint. New trays having four times the density of wells within the same footprint have already been introduced and are fast becoming the industry standard. Thus, these new trays have 16 rows and 24 columns with an adjacent well spacing of approximately 0.45 cm.

Various attempts have been made to perform multiple capillary electrophoresis simultaneously. For example, U.S. Pat. No. 6,027,627 to Li et al., the contents of which are incorporated by reference, discloses an automatic electrophoretic system which employs a capillary cartridge having a plurality of capillary tubes. The cartridge has a first array of capillary ends projecting from one side of a plate. The first array of capillary ends are spaced apart in substantially the same manner as the wells of a micro-titer tray of standard size. This allows one to simultaneously perform capillary electrophoresis on samples present in each of the wells of the tray.

U.S. Pat. No. 6,048,444 to Takahashi et al., the contents of which are incorporated by reference, discloses a capillary electrophoresis apparatus having a plurality of capillaries which are filled with migration medium and have first ends into which samples are injected and second ends from which components included in the samples are eluted. The apparatus further comprises a sheath flow cell in which the second ends are arranged in a straight line at first predetermined intervals and are terminated; means for flowing a buffer solution in the sheath flow cell from the lower part of the sheath flow cell to the upper part of the sheath flow cell; and means for detecting a component eluted from each of the capillaries in the sheath cell near the second ends.

U.S. Pat. No. 6,054,032 to Haddad et al., the contents of which are incorporated by reference, discloses a capillary electrophoresis array that includes a plurality of capillary tubes arranged adjacent each other in a generally longitudinal orientation with each of the tubes having an inlet end, an outlet end, and internal diameter no greater than about 100 microns; and a registration assembly in which adjacent tubes are held in place with a fixed lateral spacing relative to each other at both the inlet and the outlet ends of the tubes. The array is flexible along the length of the tubes.

Despite these progresses, the efficiency and reliability of capillary electrophoresis is still in need of improvement in various aspects. One particular problem is that, in many cases, and often for unknown reason, a run of capillary electrophoresis for a sample would simply fail, resulting in the waste of time and materials. Although this problem could be alleviated somewhat by running multiple analysis for the sample, in many situations, there is simply not enough sample, or the samples are too expensive, to do so using available prior art methods. Furthermore, in other situations, more electrophoresis data for a sample is desirable to achieve reliable results.

SUMMARY OF THE INVENTION

The invention provides a capillary electrophoresis system for providing simultaneous multiple analysis of a sample. The system comprises: at least one assembly of capillaries comprising a plurality of capillaries having first and second capillary ends and being held in a spaced relationship relative to one another at a point proximate to the first capillary ends, a cross-section of the first capillary ends defining a minimum bounding polygon having a footprint with a major dimension; and a container comprising at least one compartment having an opening and a bottom, and configured to hold a single body of liquid; wherein the assembly is positioned such that its first ends extend through the opening and into the at least one compartment to thereby simultaneously contact a single body of liquid, when said liquid is contained therein.

In one aspect of the above capillary electrophoresis system, the first ends of the plurality of capillaries in the capillary assembly do not contact each other. Preferably, the first ends of the plurality of capillaries are substantially parallel to each other.

In another aspect, the capillary assembly comprises two capillaries, wherein the minimum bounding polygon defined by the cross-sections of the two capillaries is a rectangle. Alternatively, the capillary assembly comprises three capillaries, wherein the minimum bounding polygon defined by the cross-sections of the three capillaries a triangle.

In yet another aspect of the capillary electrophoresis system of the present invention, the container is a one dimensional micro-titer strip and the at least one compartment is a well of said micro-titer strip. Alternatively, the container is a micro-titer tray comprising a two-dimensional array of wells, and the at least one compartment is one of said wells. Further, the system may comprise a plurality of capillary assemblies, with each assembly being positioned such that the first capillary ends of the plurality of capillaries in each assembly are inserted into a corresponding one of wells in either the one dimensional micro-titer strip or the two dimensional micro-titer array. According to an aspect of the invention, the centers of the wells are spaced apart by a distance greater than the major dimension of the cross-section of the first capillary ends in an assembly. Preferably, the major dimension is less than 4000 $\mu$m.

The capillary electrophoresis system of the present invention may further comprise an electrode that simultaneously contacts the single body of liquid together with the first ends of the plurality of capillaries of the at least one assembly. Also the system may comprise detection means to simultaneously detect the electrophoresis process in the plurality of capillaries.

In another aspect, the present invention provides an assembly of capillaries which comprises: a plurality of capillaries having first and second capillary ends and being held in a spaced relationship relative to one another at a point proximate to the first capillary ends, wherein a cross-section of the first capillary ends defines a minimum bounding polygon having a footprint with a major dimension of less than about 4000 $\mu$m.

In one embodiment of the capillary assembly, the major dimension of the minimum bounding polygon is less than about 3000 $\mu$m. In another embodiment, the major dimension of the minimum bounding polygon is less than about 2000 $\mu$m and, in yet another embodiment, the major dimension of the minimum bounding polygon is less than about 1000 $\mu$m.

In a preferred embodiment of the above capillary assembly, the capillary assembly further comprises an electrode, which is in the form of a metal wire, and that the portion of the plurality of capillaries and the metal wire are configured such that the cross-section of the plurality of capillaries and the metal wire together define the minimum bounding polygon.

In a third aspect, the present invention provides a capillary electrophoresis system for providing simultaneous multiple analysis of a sample. The system comprises: at least one assembly of capillaries comprising a plurality of capillaries having first and second capillary ends and being held in a spaced relationship relative to one another at a point proximate to the first capillary ends with a cross-section of the first capillary ends defining a minimum bounding polygon having a footprint with a major dimension; and a container comprising at least one compartment having an opening and a bottom, and configured to hold a single body of liquid; wherein the at least one assembly is positioned such that the first capillary ends extend through the opening and into the at least one compartment with each tip of said first capillary ends terminating at a height no greater than a height h above the bottom when a volume of the compartment below the height h is less than about 500 $\mu$L.

In one embodiment of this capillary electrophoresis system, the volume below the height h in the compartment is less than about 200 $\mu$L. In another embodiment, the volume is less than about 10 $\mu$L. In yet another embodiment, the volume is less than about 1 $\mu$L.

The present invention further provides a method of capillary electrophoresis for providing simultaneous multiple analysis of a sample. The method comprises: providing a container having at least one compartment having an opening and a bottom, and configured to contain a sample; inserting first ends of a plurality of capillaries that have first and second ends through the opening and into a sample contained in the compartment such that the first ends contact the sample; applying a voltage potential difference between the first and second ends to thereby cause the sample to migrate from the first ends towards the second ends within each of the plurality of capillaries; and detecting migrated portions of the sample in each of the plurality of capillaries.

In one aspect of the present invention's method, the container is a one dimensional micro-titer strip or a two dimensional micro-titer tray and the at least one compartment is a well of said micro-titer strip or tray.

In another aspect of the method, the volume of the sample is less than about 200 $\mu$L. Alternatively, the volume of the sample is less than about 10 $\mu$L or less than about 1 $\mu$L.

In yet another aspect, the present invention's method further comprises providing an electrode that simultaneously contacts the sample together with the ends of the first ends of the plurality of the capillaries.

BRIEF DESCRIPTION OF THE DRAWINGS

FIG. 3 illustrates cross-sectional views of exemplary configurations of capillaries and electrodes.

DETAILED DESCRIPTION OF THE INVENTION

Figure 1A:
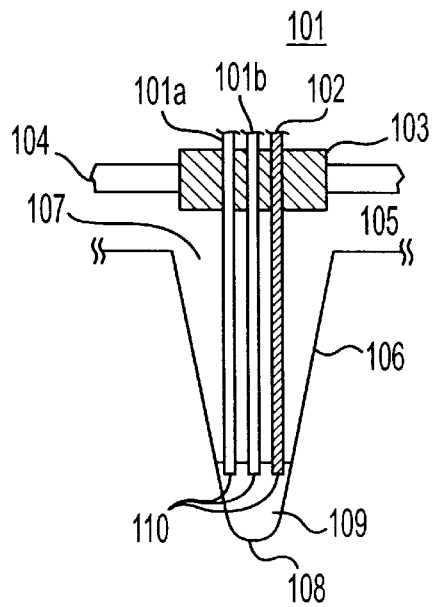
FIG. 1 illustrates a system that allows simultaneous contact of an electrophoresis sample in a well of a micro-titer tray by two capillaries and an electrode.

The present invention provides an electrophoresis system and method for multiple simultaneous analysis of a sample. Specifically, the present invention's system and method allow simultaneous access by a plurality of capillaries to a single body of electrophoresis sample, thus providing multiple simultaneous analysis of the sample without increasing the minimum required volume for such analysis. Therefore, according to the present invention, multiple simultaneous analysis of a sample is possible even if the sample amount is too small to be divided into two or more portions and analyzed separately.

In one embodiment, the present invention provides a capillary electrophoresis system for providing simultaneous multiple analysis of a sample. The system comprises (1) at least one assembly of capillaries comprising a plurality of capillaries having first and second capillary ends and being held in a spaced relationship relative to one another at a point proximate to the first capillary ends, wherein a cross-section of the first capillary ends defines a minimum bounding polygon having a footprint with a major dimension; and (2) a container comprising at least one compartment having an opening and a bottom, and configured to hold a single body of liquid; wherein the assembly is positioned such that the first capillary ends extend through the opening and into the at least one compartment to simultaneously contact a single body of liquid, when the liquid is contained in the compartment.

As used in the present invention, "capillary"0 means any capillary tube that can be used in capillary electrophoretic operations. Any capillaries suitable for performing capillary electrophoresis may be used in the present invention. These include, but are not limited to, fused silica capillary tubes. The tubes may have inner channel diameters in the range of about 20–1000 $\mu$m. Preferably, the inner channel diameters of these capillaries range from about 25 $\mu$m to about 150 $\mu$m. Furthermore, to perform an electrophoretic operation using the present invention's system, the capillaries can be filled with either conductive buffer or conductive gel, as may be required by the specific electrophoresis analysis.

As used in the present invention, an "assembly"0 of capillaries refers to any arrangement of a plurality of capillaries that satisfy the requirements of the invention. For, example, the capillaries in the assembly may be in a generally longitudinal orientation; or the capillaries may be parallel to each other only at the end portions.

As used in the present invention, a "container" refers to any device or object that is capable of holding a liquid or an electrophoresis sample. The container may have more than one compartment each configured to hold a single body of liquid. As used in the invention, "a single body of liquid"0 means a distinct volume of liquid that is not separated or partitioned by a barrier. Therefore, for example, an electrophoresis sample contained in a single well of a micro-titer strip or tray forms a single body of liquid within the meaning of the present invention. However, a sample that is divided into two or more wells does not form a single body of liquid, rather, it forms two or more distinct bodies of liquid.

According to the invention, the first ends of the plurality of capillaries may be arranged in any configuration as long as these ends, including the tips of the capillaries, can simultaneously contact a single body of liquid contained in a single compartment of a container. As used in the present invention, "capillary end"0 means not only the very tip of a capillary, but also a small length of the capillary that starts from the tip of the capillary. A person skilled in the art would understand that, in order to "take-up"0 a sample from a container, such as from a well of a micro-titer tray, the end of a capillary has to be dipped into the sample for a sufficient length, which can be determined by factors such as inner and outer diameters of the capillaries, amount and character of the sample, the shape of the container and the sample contained in it, and the method used to "take up" the sample. Methods used to transfer the sample from the compartment into the capillaries include, but are not limited to, applying a voltage potential for a specified period of time or applying a pressure difference.

In a preferred embodiment, these capillaries are arranged such that the first capillary ends in an assembly of capillaries do not contact each other. Among other things, this feature allows easy cleaning of the capillaries between runs and avoids problems caused by statics. More preferably, the first ends of the plurality of capillaries are substantially parallel to each other.

The plurality of capillaries of the present invention may comprise any number of capillaries as determined by the specific requirements of a particular electrophoresis analysis. In one preferred embodiment, the plurality of capillaries comprises two capillaries. In another preferred embodiment, it comprises three capillaries. The configurations of these capillaries will be discussed in detail below.

The container of the present invention's system can be any container having at least one compartment configured to hold a single body of liquid. For example, a single or a plurality of test tubes; or a single or a plurality of micro test tubes may be used as the container in the present invention. As used in the invention, a "micro test tube" refers to vials generally having a reverse conical shape and can contain up to 1 mL of liquid. As understood by persons skilled in the art micro test tubes include micro centrifuge tubes, micro freezing tubes, and micro container tubes. The container of the present invention may also be customly made, such as a substrate having a plurality of wells each designed to contain a specific amount of liquid.

In a preferred embodiment, the container is either a one-dimensional (strip) or a two-dimensional (tray) micro-titer array of wells and that at least one compartment is one of the wells. More preferably, the system of the present invention may comprise a plurality of capillary assemblies, with each assembly being positioned such that the first capillary ends of the plurality of capillaries in an assembly are inserted into a corresponding one of wells in either the micro-titer strip or tray. According to an aspect of the invention, the centers of the wells are spaced apart by a distance greater than the major dimension of the cross-section of the first capillary ends in an assembly. Preferably, the major dimension defined by the cross-sections of the first capillaries of the plurality of capillaries in an assembly is less than 4000 $\mu$m. This embodiment allows the plurality of capillaries to simultaneously access and contact a relatively small amount of sample in the form of a small volume.

The capillary electrophoresis system of the present invention may further comprise an electrode that simultaneously contacts the single body of liquid together with the first ends of the plurality of capillaries. The electrode may be separately arranged to access the liquid, such as from the bottom of the compartment. Preferably, especially when using a metal wire as the electrode, the electrode is arranged together and in the same manner as the plurality of capillaries in an assembly. In this embodiment, the electrode is treated just as another one of the plurality of capillaries so that the end of the electrode simultaneously contacts the liquid with the first capillary ends.

The present invention's system may also comprise detection means to simultaneously detect the electrophoresis process in the plurality of capillaries. Any conventional means for capillary electrophoresis process may be used in the system of the present invention. For example, detection means disclosed in U.S. Pat. No. 6,027,627, the contents of which are incorporated by reference, may be used in the present invention's system. However, in the present invention, the detection means includes a mechanism for distinguishing the plurality of capillaries to a single compartment from capillaries to other compartments, as well as distinguishing each capillary from others. This can be done, for example, by processing data from the plurality of capillaries in a single assembly (from a single well) first, followed by processing data from different assemblies.

FIG. 1 illustrates a system that allows simultaneous contact of an electrophoresis sample in a well of a micro-titer tray by two capillaries and an electrode. As shown in FIG. 1A, capillary assembly 101 comprises two capillaries 101A and 101B and electrode 102. The capillaries 101 and electrode 102 are arranged and held substantially parallel to, but spaced apart from, each other by a holder 103, which is an integrated part of a plate member 104. Container 105 is a micro-titer tray (only partially shown) which has a plurality of wells 106, each of which has an opening 107 and a bottom 108. An electrophoresis sample 109 is contained in the well 106. Capillaries 101 and electrode 102 are configured such that they can be lowered into well 106 through opening 107 towards bottom 108 such that the first capillary ends and the tip of the electrode, collectively 110, simultaneously contact sample 109. As shown in FIG. 1A, the first capillary ends and the tip of the electrode are below the surface of sample 107.

Figure 1B:
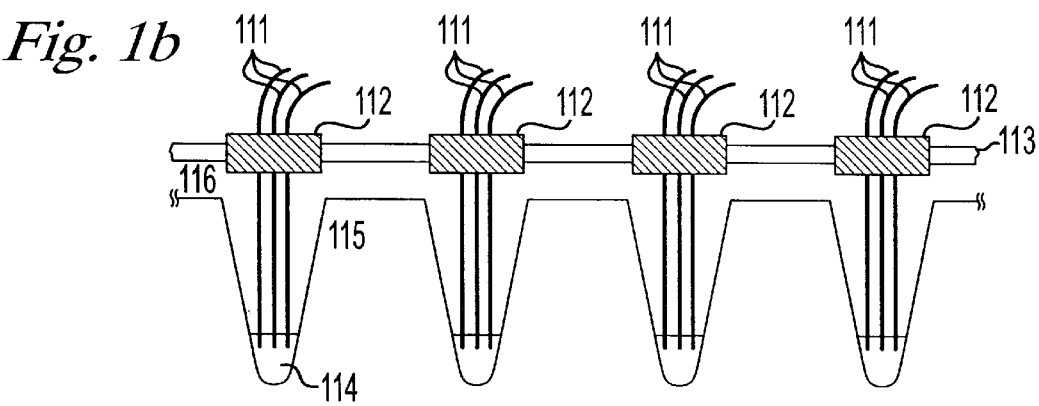
Figure 1C:
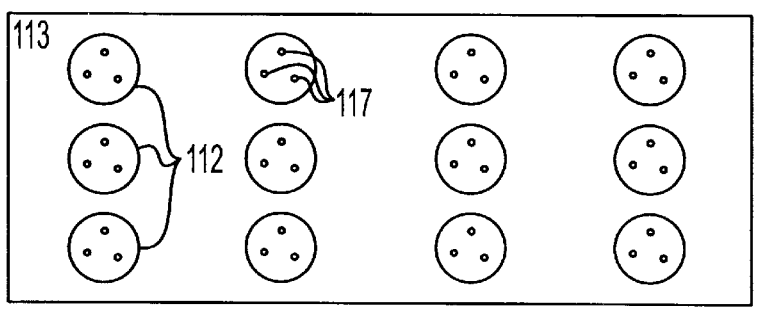
Figure 1D:
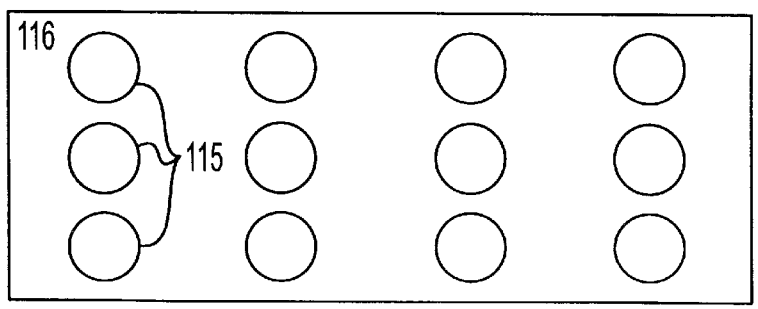

FIG. 1B illustrates a sectional-view of a plurality of capillary assemblies each inserted into a corresponding one of the wells in a micro-titer tray. Capillary assemblies 111 are held by holders 112 contained in plate member 113. The plurality of capillaries and, optionally electrode, in each of the assembly 111 are configured to simultaneously contact a sample 114 in a well 115. The plurality of capillary assemblies 111 are configured to correspond to the wells 115 of micro-titer tray 116. FIG. 1C is a plan view of the plate member 113 with a two-dimensional array of holders 112 (capillaries or electrode not shown). Each holder 112 comprises holes/lumen 117, in which capillaries and electrode are held. FIG. 1D is a plan view of micro-titer tray 116 having a two-dimensional array of wells 115. Each of holders 112 corresponds to a well 115 such that the plurality of capillaries held by each holder simultaneously contact a sample in a well.

Figure 2A:
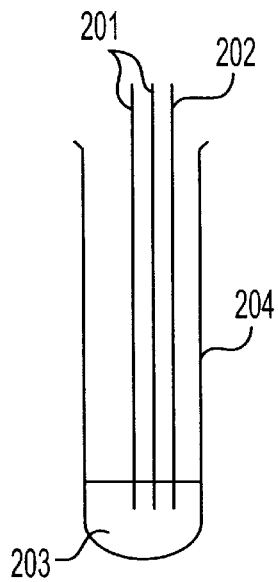
FIG. 2 illustrates three additional types of containers that may be used in the present invention.
Figure 2B:
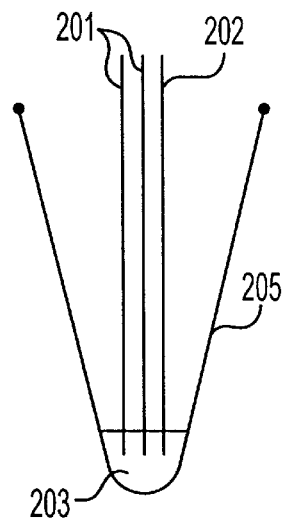
Figure 2C:
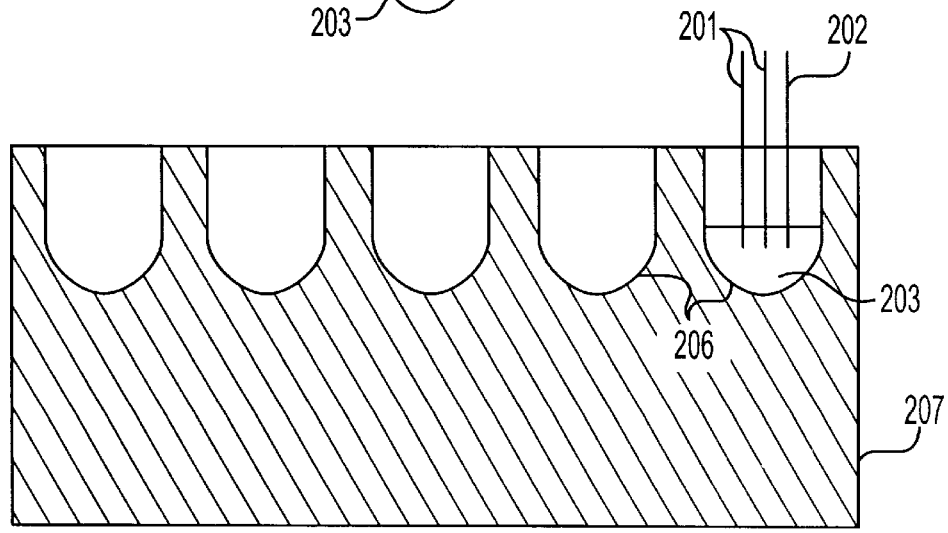

FIG. 2 illustrates three additional types of containers that may be used in the present invention. As shown in FIG. 2, two capillaries 201 and an electrode 202 simultaneously contact a sample 203 in a regular test tube 204 (FIG. 2A); in a micro test tube 205 (FIG. 2B); and in one of the wells 206 of a custom made container 207.

In another embodiment, the present invention provides an assembly of capillaries which comprises a plurality of capillaries having first and second capillary ends and being held in a spaced relationship relative to one another at a point proximate to the first capillary ends with a cross-section of the first capillary ends defining a minimum bounding polygon having a footprint with a major dimension of less than about 4000 $\mu$m. Therefore, this embodiment specifies that the plurality of capillaries are arranged such that the specified dimension requirement is satisfied.

FIGS. 3A–3H illustrate cross-sectional views of exemplary configurations of capillaries and electrodes. FIG. 3A shows the cross-sections of two capillaries, in which the minimum bounding polygon defined by the cross-sections is a rectangle. FIG. 3B shows the cross-sections of two capillaries and an electrode, in which the minimum bounding polygon defined by the cross-sections is a triangle. FIG. 3C shows the cross-section of two capillaries and an electrode, in which the minimum bounding polygon defined by the cross-sections is a rectangle. FIG. 3D shows the cross-sections of three capillaries and an electrode, in which the minimum bounding polygon defined by the cross-sections is a rectangle. FIG. 3E shows the cross-section of three capillaries and an electrode, in which the minimum bounding polygon defined by the cross-sections is a triangle. Figure 3F shows the cross-section of three capillaries and an electrode, in which the minimum bounding polygon defined by the cross-sections is a quadrangle. FIG. 3G shows the cross-section of three capillaries and an electrode, in which the minimum bounding polygon defined by the cross-sections is a triangle. FIG. 3H shows the cross-section of four capillaries and an electrode, in which the minimum bounding polygon defined by the cross-sections is a pentagon.

As illustrated in FIGS. 3A–3H, the electrode and the plurality of capillaries in a capillary assembly can be arranged many ways. In this particular embodiment, however, the invention specifies the arrangements by the minimum bounding polygons defined by the cross-sections of the capillaries and electrode. Specifically, the major dimension of the footprint of the minimum bounding polygon is less than about 4000 $\mu$m. As used in the present invention, the major dimension of a footprint refers to the longest distance between any two points on the perimeter of the polygon. For example, the major dimension of a triangle is the dimension of its longest side, the major dimension of a rectangle is its diagonal, and the major dimension of a quadrangle is the longer of the two slanted lines between its two pairs of opposite angles. FIGS. 3A–3H show the major dimension, MD, of each of the polygons defined by the cross-sections of the capillaries and electrode in each of the configurations.

In one embodiment of this capillary electrophoresis system, the major dimension of the minimum bounding polygon is less than about 3000 $\mu$m. In another embodiment, the major dimension is less than about 2000 $\mu$m and, in yet another embodiment, the major dimension of the minimum bounding polygon is less than about 1000 $\mu$m.

The different configurations of the capillaries and the electrode can be further defined by the area of the footprint of the minimum bounding polygons. As used in the present invention or understood by one skilled in the art, the footprint is the area bounded by the perimeter of the polygon. For example, in FIG. 3D, the footprint for the cross-sections of the three capillaries and one electrode is the area occupied by the rectangle. Thus, in order for the capillaries and the electrode to simultaneously contact a sample at the bottom of a well of a micro-titer tray, the footprint of the capillaries and the electrode, or the area of the rectangle, should be smaller than the opening of the well.

In a third embodiment, the present invention provides a capillary electrophoresis system that comprises: (1) at least one assembly of capillaries comprising a plurality of capillaries having first and second capillary ends and being held in a spaced relationship relative to one another at a point proximate to the first capillary ends with a cross-section of the first capillary ends defining a minimum bounding polygon having a footprint with a major dimension; and (2) a container comprising at least one compartment having an opening and a bottom, and configured to hold a single body of liquid; wherein the at least one assembly is positioned such that the first capillary ends extend through the opening and into the at least one compartment with each tip of said first capillary ends terminating at a height no greater than a height h above the bottom, wherein a volume of the compartment below the height h is less than about 500 $\mu L$. Therefore, in this embodiment, the configuration of the capillaries and the container is defined by the volume of liquid that the plurality of capillaries can simultaneously access in the compartment of the container.

Figure 4:
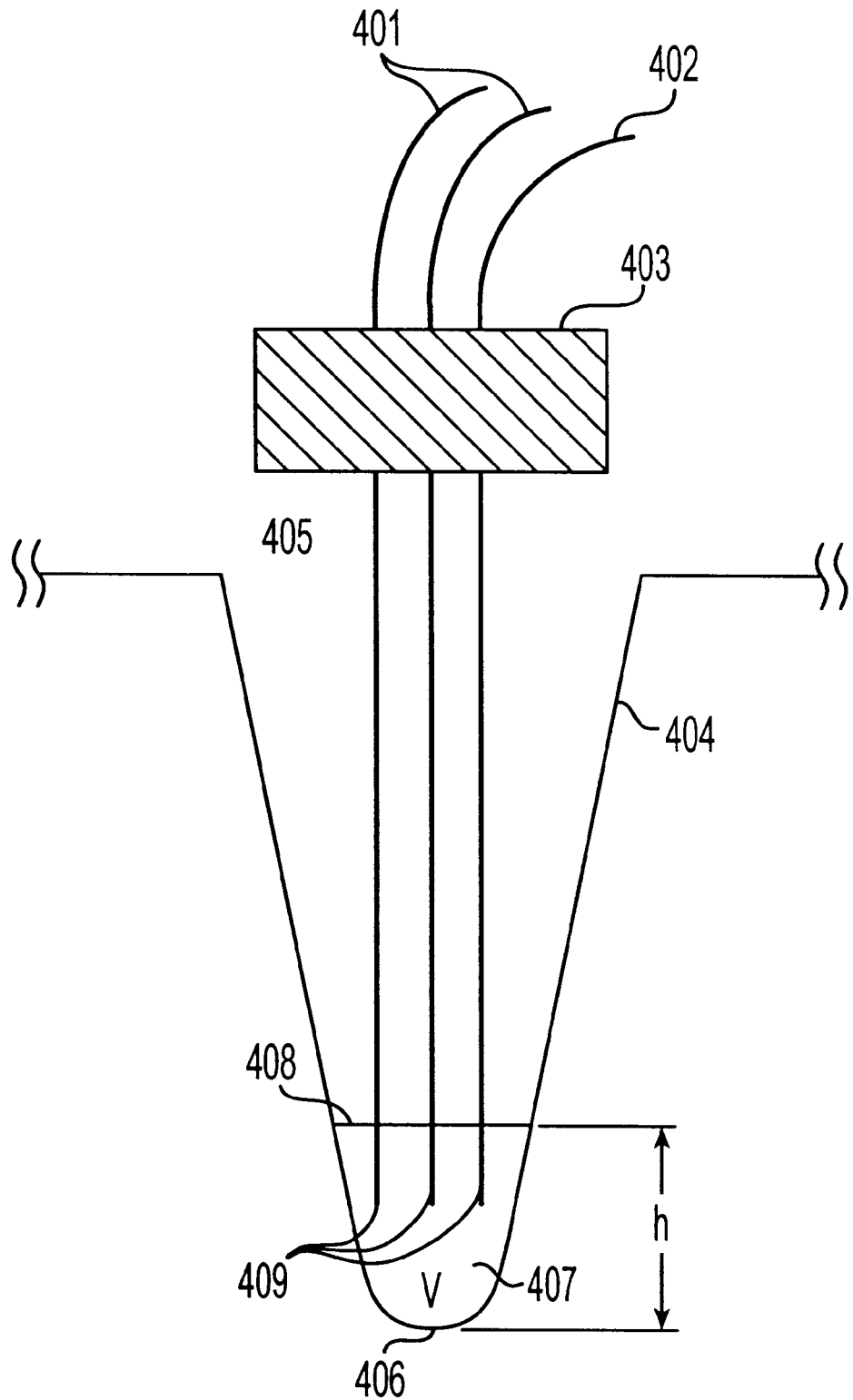
FIG. 4 illustrates a sample in a well of a micro-titer tray that can be simultaneously contacted by two capillaries and an electrode.

FIG. 4 illustrates a sample in a well of a micro-titer tray that can be simultaneously contacted by two capillaries and an electrode. Capillaries 401 and electrode 402 are substantially parallel to each other and held by holder 403. Sample well 404 comprise opening 405 and bottom 406, which contains ample 407. The distance between bottom 406 and the surface 408 of sample 407 is h. The volume V of the well between surface 408 and bottom 406 is less than about 500 $\mu L$. Capillaries 401 and electrode 402 are lowered into well 404 through opening 405 such that the distance between the uppermost of their tips and the bottom 406 is less than h, which means the ends of the capillaries and the electrode are below the surface 408 of sample 407.

In one embodiment of this capillary electrophoresis system, the volume V defined by surface 408 and bottom 406 is less than about 200 $\mu L$. In another embodiment, the volume V is less than about 10 $\mu L$. In yet another embodiment, the volume V is less than about 1 $\mu L$.

The present invention further provides a method of capillary electrophoresis for providing simultaneous multiple analysis of a sample. The method comprises: (1) providing a container having at least one compartment having an opening and a bottom, and configured to contain a sample; (2) inserting first ends of a plurality of capillaries that have first and second ends through the opening and into a single body sample contained in the compartment such that the first ends contact the sample; (3) applying a voltage potential difference between the first and second ends to thereby cause the sample to migrate from the first ends towards the second ends within each of the plurality of capillaries; and (4) detecting migrated portions of the sample in each of the plurality of capillaries.

The present invention's method can be used in combination with a variety of conventional capillary electrophoresis systems and methods, such as automated multiple sample delivery system and detection systems for multiple capillaries.

In a preferred embodiment, the present invention's method comprises a step of inserting the first ends of the plurality of capillaries into a well of either a one-dimensional micro-titer strip or a two-dimensional micro-titer tray. Therefore, the method of the present invention allows for electrophoretic analysis of multiple samples, with each of the samples being simultaneously electrophoretically analyzed by a plurality of capillaries.

In one aspect, the method of the present invention further comprises a step of introducing a sample having a volume of less than about 200 $\mu L$ into the at least one compartment. In another aspect of the method, the volume of the sample is less than about 10 $\mu L$ and, in yet another aspect of the method, the volume of the sample is less than about 1 $\mu L$.

Therefore, the present invention's method allows multiple analysis of an amount of sample that may not be sufficient for multiple analysis using separate compartment.

In yet another preferred embodiment, the present invention's method further comprises providing an electrode that simultaneously contacts the electrophoresis sample together with the ends of the plurality of capillaries. The electrode may be provided in various ways to the sample, although, preferably, the electrode is held together with the plurality of the capillaries.

While the present invention has been described with reference to the above specific and preferred embodiments, it should be noted that the scope of the invention is not limited to these examples. One skilled in the art may find variations of these embodiments that fall within the spirit of the present invention, the scope of which is defined by the claims set forth below.

What is claimed is:

1. A capillary electrophoresis system for providing simultaneous multiple analysis of a sample, said system comprising:

at least one assembly of capillaries, said at least one assembly comprising a plurality of capillaries having first and second capillary ends and being held in a spaced relationship relative to one another at a point proximate to said first capillary ends, a cross-section of said first capillary ends defining a minimum bounding polygon having a footprint, the footprint having a major dimension; and a container comprising at least one compartment having an opening and a bottom, and configured to hold a single body of liquid;

wherein said at least one assembly is positioned such that the first capillary ends of said plurality of capillaries extend through said opening and into said at least one compartment to thereby simultaneously contact a single body of liquid, when said liquid is contained therein.

2. The capillary electrophoresis system of claim 1, wherein the first capillary ends of said plurality of capillaries in said at least one assembly do not contact each other.

3. The capillary electrophoresis system of claim 2, wherein first capillary ends are substantially parallel to each other.

4. The capillary electrophoresis system of claim 1, wherein the at last one assembly comprises two capillaries and said footprint is a rectangle.

5. The capillary electrophoresis system of claim 1, wherein the at last one assembly comprises three capillaries and said footprint is a triangle.

6. The capillary electrophoresis system of claim 1, wherein the container is a micro-titre strip comprising a one-dimensional array of wells, and the at least one compartment is one of said wells.

7. The capillary electrophoresis system of claim 1, wherein the container is a micro-titer tray comprising a two-dimensional array of wells, and the at least one compartment is one of said wells.

8. The capillary electrophoresis system of either claim 6 or claim 7, comprising a plurality of assemblies, each assembly being positioned such that the first capillary ends of said plurality of capillaries in said assembly are inserted into a corresponding one of said wells.

9. The capillary electrophoresis system of claim 8, wherein centers of said wells are spaced apart by distance greater than said major dimension.

10. The capillary electrophoresis system of claim 9, wherein said major dimension is less than about 4000 µm.

11. The capillary electrophoresis system of claim 1, wherein the assembly further comprises an electrode which also simultaneously contacts said single body of liquid.

12. A capillary electrophoresis system for providing simultaneous multiple analysis of a sample, said system comprising:

at least one assembly of capillaries, said at least one assembly comprising a plurality of capillaries having first and second capillary ends and being held in a spaced relationship relative to one another at a point proximate to said first capillary ends, a cross-section of said first capillary ends defining a minimum bounding polygon having a footprint, the footprint having a major dimension; and a container comprising at least one compartment having an opening and a bottom, and configured to hold a single body of liquid;

wherein said at last one assembly is positioned such that said first capillary ends of said plurality of capillaries in said assembly extend through said opening and into said at least one compartment with each tip of said first capillary ends terminating at a height no greater than a height h above the bottom of said compartment when a volume of said compartment below said height h is less than about 500 µL.

13. The capillary electrophoresis system of claim 12, wherein the volume is less than about 200 µL.

14. The capillary electrophoresis system of claim 13, wherein the volume is less than about 10 µL.

15. The capillary electrophoresis system of claim 14, wherein the volume is less than about 1 µL.

16. A method of capillary electrophoresis for providing simultaneous multiple analysis of a sample, said method comprising:

providing a container having at least one compartment, said compartment having an opening and a bottom, and being configured to contain a sample;

inserting first ends of a plurality of capillaries having first and second ends through said opening and into a sample contained in said compartment such that said first ends contact said sample;

applying a voltage potential difference between said first and second ends to thereby cause said sample to migrate from said first ends towards said second ends within each of said plurality of capillaries; and individually detecting migrated portions of said sample in each of said plurality of capillaries to thereby simultaneously obtain a plurality of separate analyses of said sample.

17. The method of claim 16, comprising inserting the first ends of said plurality of capillaries into a well of either a one-dimensional micro-titre strip or a two-dimensional micro-titre tray.

18. The method of claim 16, further comprising a step of introducing a sample having a volume of less than about 200 µL into the at least one compartment.

19. The method of claim 18, wherein the volume of the sample is less than about 10 µL.

20. The method of claim 18, wherein the volume of the sample is less than about 1 µL.

21. The method of claim 16, further comprising a step of inserting an electrode into said compartment along with said first ends of said plurality of capillaries such that the electrode also contacts said sample.

22. A method of capillary electrophoresis for providing simultaneous multiple analysis of a sample, said method comprising:

providing a container having at least one compartment, said compartment having an opening and a bottom, and being configured to contain a sample;

providing a plurality of capillaries having first and second ends, the capillaries being held in a spaced relationship relative to one another at a point proximate to said first ends;

inserting the first ends through said opening and into a sample contained in said compartment such that said first ends contact said sample;

applying a voltage potential difference between said first and second ends to thereby cause said sample to migrate from said first ends towards said second ends within each of said plurality of capillaries; and detecting migrated portions of said sample in each of said plurality of capillaries.

23. The method of claim 22, comprising inserting the first ends of said plurality of capillaries into a well of either a one-dimensional micro-titre strip or a two-dimensional micro-titre tray.

24. The method of claim 22, further comprising a step of introducing a sample having a volume of less than about 200 µL into the at least one compartment.

25. The method of claim 22, wherein the volume of the sample is less than about 10 µL.

26. The method of claim 22, wherein the volume of the sample is less than about 1 µL.

27. The method of claim 22, comprising individually detecting migrated portions of said sample in each of said plurality of capillaries to thereby simultaneously obtain a plurality of separate analyses of said sample.

* * * * *